(12) United States Patent  
Palma et al.

(10) Patent No.: US 12,033,336 B2
(45) Date of Patent: Jul. 9, 2024

(54) DEFORMABLE REGISTRATION OF MEDICAL IMAGES

(71) Applicant: MERATIVE US L.P., Ann Arbor, MI (US)

(72) Inventors: Giovanni John Jacques Palma, Chaville (FR); Greg Padiasek, Mississauga (CA)

(73) Assignee: MERATIVE US L.P., Ann Arbor, MI (US)

( * ) Notice: Subject to any disclaimer, the term of this patent is extended or adjusted under 35 U.S.C. 154(b) by 390 days.

(21) Appl. No.: 17/402,247

(22) Filed: Aug. 13, 2021

(65) Prior Publication Data

US 2023/0052401 A1    Feb. 16, 2023

(51) Int. Cl.
*G06T 7/33*    (2017.01)
*G06N 20/00*    (2019.01)
(Continued)

(52) U.S. Cl.
CPC .................. *G06T 7/33* (2017.01); *G06T 7/13* (2017.01); *G16H 30/40* (2018.01); *G06N 20/00* (2019.01);
(Continued)

(58) Field of Classification Search
CPC ......... G06T 7/33; G06T 7/13; G06T 2200/04; G06T 2207/10081; G06T 2207/10088; G06T 2207/20081; G06T 2207/20132; G06T 2207/30056; G06T 2207/30096; G06T 2207/10072; G16H 30/40; G16H 50/20; G06N 20/00; G06N 3/04; G06N 3/08
See application file for complete search history.

(56) References Cited

U.S. PATENT DOCUMENTS 10,593,051 B2    3/2020   Park et al.
2007/0167784 A1*  7/2007   Shekhar .................. A61B 6/032
                                                600/443
(Continued)

OTHER PUBLICATIONS

Anonymous, "Deformation estimation by surface tracking", 2007, 6 pages.
Collins et al., "Improving Registration Robustness for Image-Guided Liver Surgery in a Novel Human-to-Phantom Data Framework", IEEE, 2017, 10 pages.
(Continued)

*Primary Examiner* — Umair Ahsan
(74) *Attorney, Agent, or Firm* — Michael Best & Friedrich LLP (57) ABSTRACT

Systems and computer-implemented methods of performing image registration. One method includes receiving a first image and a second image acquired from a patient at different times and, in each of the first image and the second image, detecting an upper boundary of an imaged object in an image coordinate system and detecting a lower boundary of the imaged object in the image coordinate system. The method further includes, based on the upper boundary and the lower boundary of each of the first image and the second image, cropping and padding at least one of the first image and the second image to create an aligned first image and an aligned second image and executing a registration model on the aligned first image and the aligned second image to compute a deformation field between the aligned first image and the aligned second image.

16 Claims, 7 Drawing Sheets

(51) Int. Cl.
  *G06T 7/13* (2017.01)
  *G16H 30/40* (2018.01)
(52) U.S. Cl.
  CPC .............. *G06T 2200/04* (2013.01); *G06T 2207/10081* (2013.01); *G06T 2207/10088* (2013.01); *G06T 2207/20081* (2013.01); *G06T 2207/20084* (2013.01); *G06T 2207/20132* (2013.01); *G06T 2207/30056* (2013.01); *G06T 2207/30096* (2013.01)

(56) References Cited

U.S. PATENT DOCUMENTS

2008/0267483 A1* 10/2008 Zhan .............. G06V 10/24
  382/131
2021/0192758 A1* 6/2021 Song ............. G06T 7/32

OTHER PUBLICATIONS

Dalca et al., "Unsupervised Learning for Fast Probabilistic Diffeomorphic Registration", arXiv, 2018, 10 pages.
Hu et al., "Weakly-supervised convolutional neural networks for multimodal image registration", Medical Image Analysis, 2018, vol. 49, pp. 1-13.
Muller et al., "Automatic Multi-modal ToF/CT Organ Surface Registration", Conference Paper, 2011, 5 pages.
Rohe et al., "SVF-Net: Learning Deformable Image Registration Using Shape Matching", 2017, Medical Image Computing and Computer Assisted Intervention, pp. 266-274.
Selka et al., "Surface parameterization and registration for statistical multiscale atlasing of organ development", IEEE Conference on Computer Vision and Pattern Recognition Workshops, 2019, pp. 134-139.

* cited by examiner

DEFORMABLE REGISTRATION OF MEDICAL IMAGES

FIELD

Embodiments described herein relate to systems and methods for performing deformable registration of medical images, such as, for example, liver three-dimensional (3D) computed tomography (CT) images.

SUMMARY

Image registration generally refers to transforming different images into a common coordinate system, which allows the registered images to be more easily and accurately analyzed and compared. For example, image registration is often performed for medical images acquired from the same patient, wherein the images are acquired at different times. For example, registration can be performed to compensate for patient positioning and movement during an imaging procedure or scan. Image registration is commonly used in clinical settings to diagnose various medical conditions, such as, for example, to diagnose and track liver tumors within computed tomography (CT) images.

In surface-based liver registration, the liver surface is registered without considering the internal liver volume. This procedure is problematic, however, when a CT scan does not include complete liver volumes. In such cases, a partial liver image may be stretched to fit a surface of a complete liver in another CT scan. This stretching results in an incorrect registration of a partial liver. Another problem associated with surface-based liver registration is that tumors located in the liver or on the liver surface may not be registered optimally, which may have an impact on tumor tracking.

Accordingly, embodiments described herein provide methods and systems for performing image registration by aligning common liver regions and landmarks within the regions while ignoring missing liver regions. This image registration can be based on a deep learning model trained using a dataset of training images, such as, for example, CT images, wherein the training is based on liver landmarks in addition to liver surfaces. Once trained, the model can detect liver regions missing in a scan and can focus the registration on common liver regions.

In particular, some embodiments described herein provide a computer-implemented method of performing image registration. The method includes receiving a first image and a second image acquired from a patient at different times and, in each of the first image and the second image, detecting an upper boundary of an imaged object in an image coordinate system and detecting a lower boundary of the imaged object in the image coordinate system. The method further includes, based on the upper boundary and the lower boundary of each of the first image and the second image, cropping and padding at least one of the first image and the second image to create an aligned first image and an aligned second image and executing a registration model on the aligned first image and the aligned second image to compute a deformation field between the aligned first image and the aligned second image.

Other embodiments described herein provide a system for performing image registration. The system includes an electronic processor. The electronic processor is configured to receive a first image and a second image, the first image and the second image acquired from a patient at different times, and, in each of the first image and the second image, detect an upper boundary of an imaged object in an image coordinate system and detect a lower boundary of the imaged object in the image coordinate system. The electronic processor is also configured to, based on the upper boundary and the lower boundary of each of the first image and the second image, crop and pad at least one of the first image and the second image to create an aligned first image and an aligned second image, and execute a registration model on the aligned first image and the aligned second image to compute a deformation field between the aligned first image and the aligned second image.

Additional embodiments described herein provide non-transitory computer readable medium storing instructions that, when executed by an electronic processor, perform a set of functions. The set of functions includes receiving a first image and a second image, the first image and the second image acquired from a patient at different times and, in each of the first image and the second image, detecting an upper boundary of an imaged object in an image coordinate system and detecting a lower boundary of the imaged object in the image coordinate system. The set of functions also includes, based on the upper boundary and the lower boundary of each of the first image and the second image, cropping and padding at least one of the first image and the second image to create an aligned first image and an aligned second image, and executing a registration model on the aligned first image and the aligned second image to compute a deformation field between the aligned first image and the aligned second image.

Other aspects of the embodiments will become apparent by consideration of the detailed description and accompanying drawings.

DETAILED DESCRIPTION

Before any embodiments are explained in detail, it is to be understood that the embodiments are not limited in their application to the details of construction and the arrangement of components set forth in the following description or illustrated in the following drawings. Other embodiments are capable of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or coupling, whether direct or indirect. Also, electronic communications and notifications may be performed using any known means including direct connections, wireless connections, etc.

A plurality of hardware and software-based devices, as well as a plurality of different structural components may be utilized to implement the embodiments. In addition, embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the embodiments may be implemented in software (e.g., stored on non-transitory computer-readable medium) executable by one or more processors. As such, it should be noted that a plurality of hardware and software-based devices, as well as a plurality of different structural components, may be utilized to implement the embodiments. For example, "computing device" and "server" as described in the specification may include one or more electronic processors, one or more memory modules including non-transitory computer-readable medium, one or more input/output interfaces, and various connections (e.g., a system bus) connecting the components.

Figure 1:
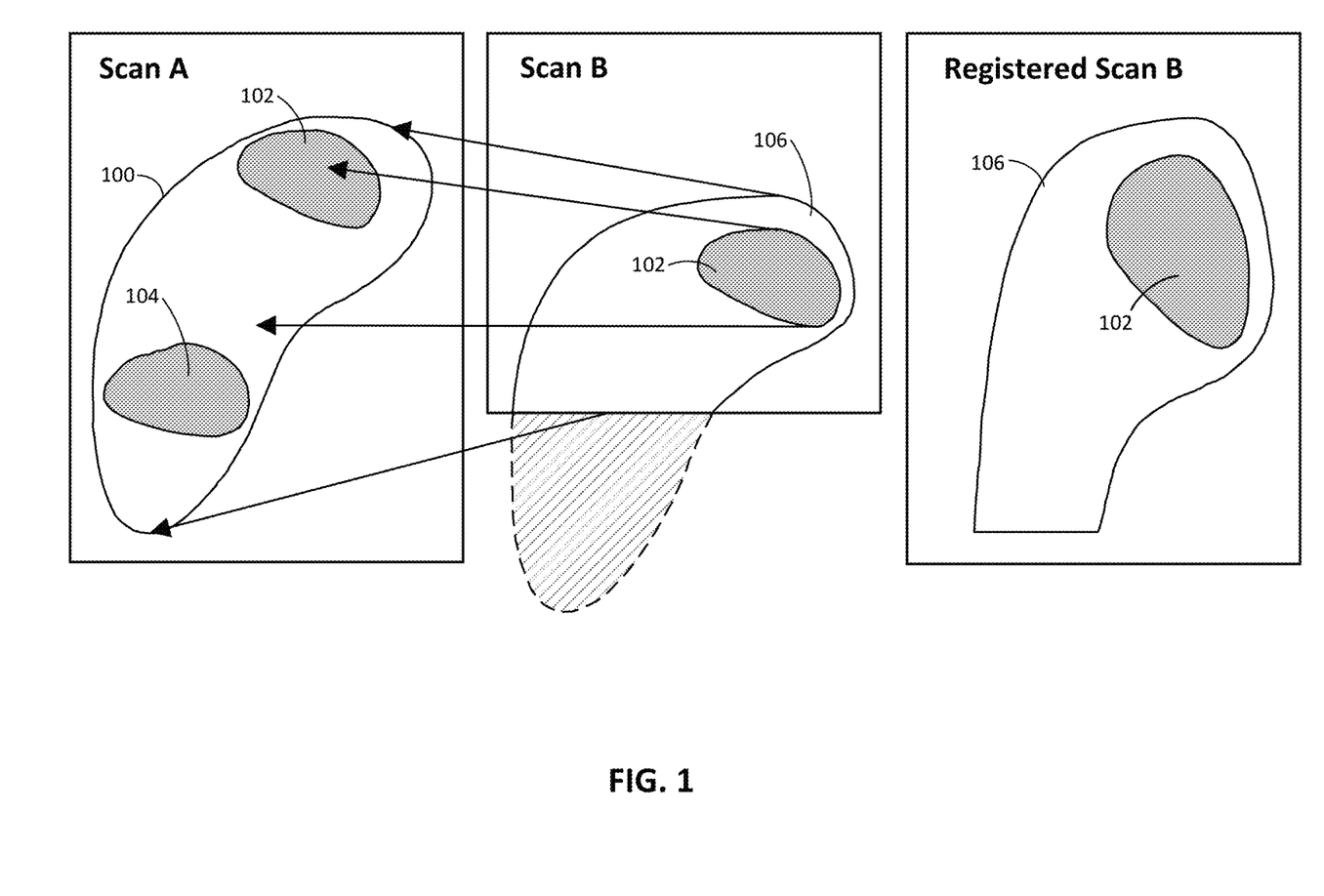
FIG. 1 illustrates an example of performing surface-based image registration.

As described above, surface-based image registration can cause distortion and make it difficult to accurate track tumors. For example, FIG. 1 illustrates two computed tomography (CT) scans (Scan A and Scan B) of a patient's liver. Scan A captured a full liver volume 100, which includes a first lesion 102 and a second lesion 104. In comparison, Scan B captured an incomplete liver volume 106, which only includes the first lesion 102. As illustrated in FIG. 1, using surface-based liver registration, the internal region of Scan B is forced to follow the internal region of Scan A, regardless of the lesions (or other landmarks) present within these regions. In particular, the incomplete liver volume 106 from Scan B is stretched to fit the complete liver volume 100 from Scan A, which distorts the first lesion 102 in the Registered Scan B and, thus, produces an inaccurate image of the lesions within the patient's liver. The below loss function, which includes a Dice coefficient, captures the loss or error between Scan A and Registered Scan B, where D is the deformation field, A is the volume of the liver in Scan A, and B is the volume of the liver in Scan B.

$$\text{Loss} = \text{DICE}(\text{Reg}(B), A) + \|\nabla D\|$$

Accordingly, to address these and other issues with image registration, embodiments herein provide systems and methods for performing deformable registration of medical images that compensates for patient positioning and movement while considering the internal organ volume to yield an optimally registered organ that accurately tracks a lesion, such as liver lesions.

Figure 2:
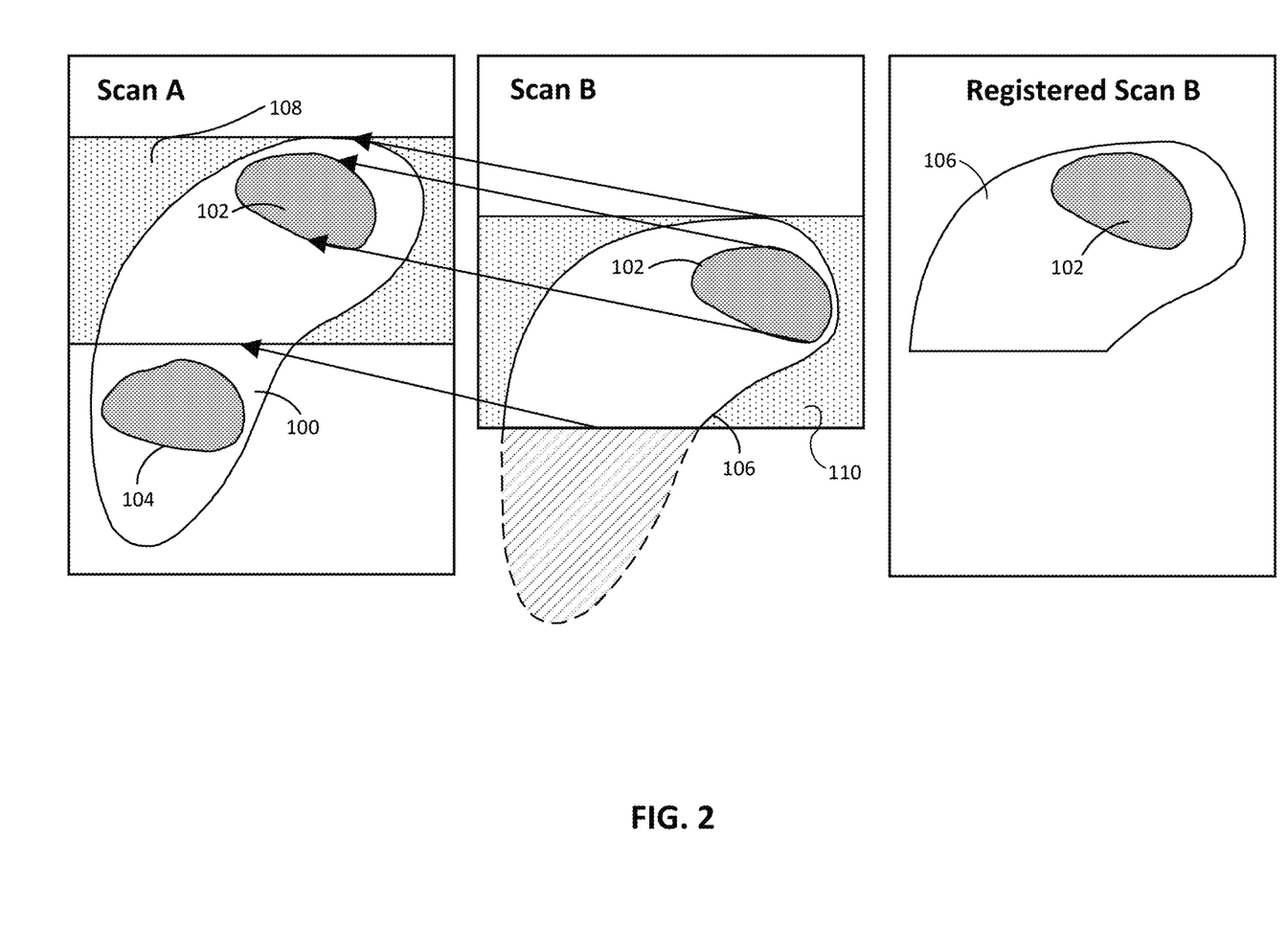
FIGS. 2 and 3 illustrates an example of performing image registration using a common liver region according to some embodiments.
Figure 3:
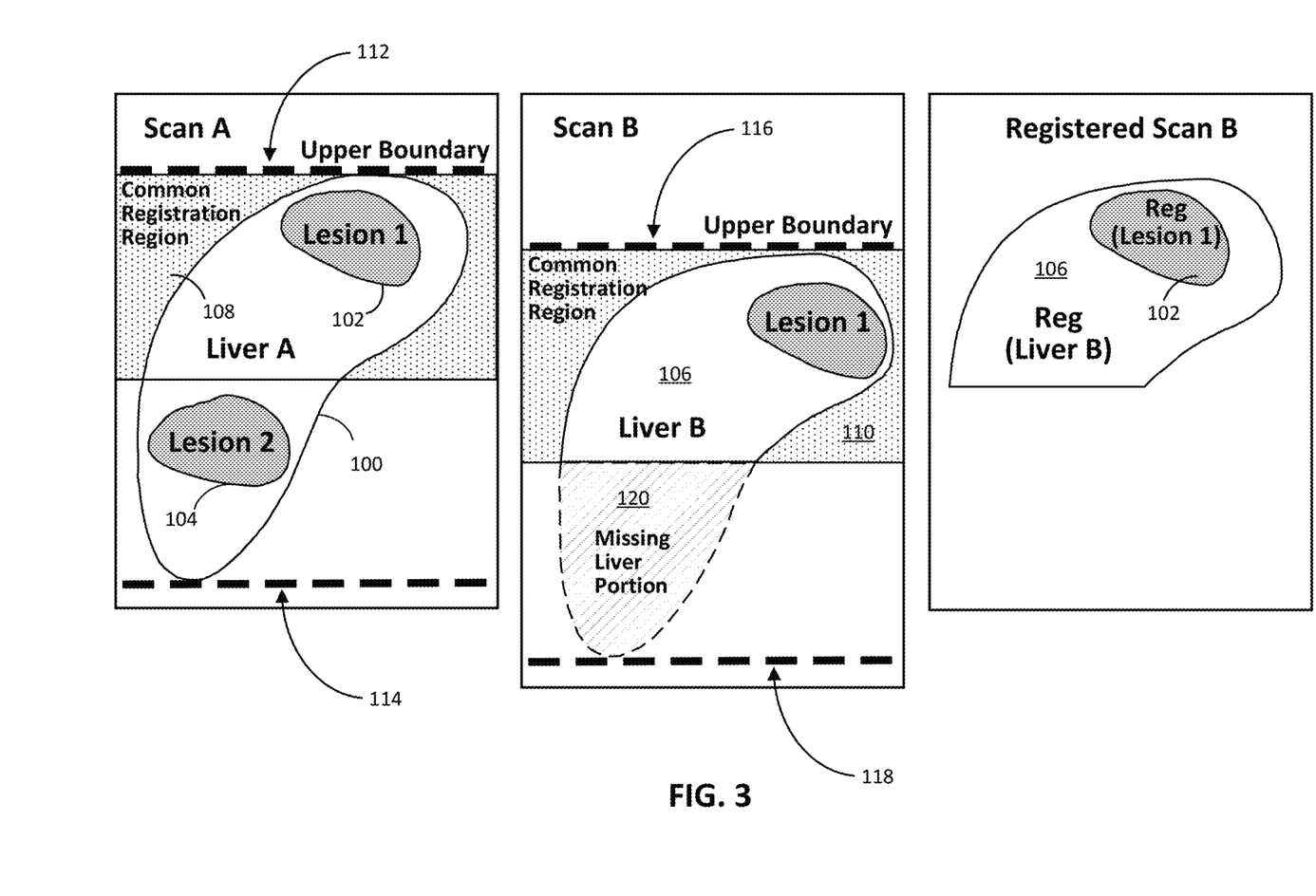

For example, FIGS. 2 and 3 illustrates an example of performing image registration using a common liver region according to some embodiments. As illustrated in FIGS. 2 and 3, using the same CT scans as used in FIG. 1, a Registered Scan B is produced using the common liver volume between Scan B and Scan A (i.e., regions 108 and 110 in Scan A and Scan B, respectively) as well as the matching lesion 102 within this common liver volumes 108 and 110. In particular, as illustrated in FIG. 3, to identify the common volumes or regions 108 and 110, an upper boundary 112 and a lower boundary 114 of the liver volume 100 in Scan A are identified as well as an upper boundary 116 and a lower boundary 118 of the liver volume 106 in Scan B. These boundaries can be used to align the liver volumes in both images and identify a missing liver portion 120 between the two scans (e.g., in Scan B) and, consequently, identify the common regions 108 and 110. As illustrated in FIG. 3, the liver volume 106 may extend past the bounds of the CT scan, as evidenced by the missing liver portion 120. In this situation, the missing liver portion 120 is derived from the physical upper and lower boundary estimates (e.g., the upper boundary 116 and the lower boundary 118) of the liver of Scan B.

Thus, as compared to Registered Scan B illustrated in FIG. 1 (produced using surface-stretching), Registered Scan B illustrated in FIGS. 2 and 3 provides a more accurate representation of the lesion 102 by recognizing the missing liver volume in Scan B and using liver landmarks to perform the registration. In other words, using the image registration procedure described herein, liver landmarks are identified and missing liver regions are detected, such that the registering is focused on the common liver regions found in Scan A and Scan B and matching landmarks within these regions. As described in more detail below, the liver landmarks can include an outer surface of the liver, an outer surface of a lesion, the bounds or extent of the captured liver volume, or other identifiable landmarks associated with the liver, the lesion, or both.

The below loss function can be used with the image registration illustrated in FIGS. 2 and 3, where D is the deformation field, $A_c$ and $B_c$ are common liver volume A and common liver volume B, respectively (i.e., regions 108 and 110), and $L^i_A$ and $L^i_B$ are i-th lesion in common liver volume A and i-th lesion in common liver volume B, respectively. Accordingly, this loss function focuses on the common volumes between the scans as well as the lesions within these common volumes. In particular, the below loss function includes both a common liver Dice coefficient as well as a common lesion Dice coefficient.

$$\text{Loss} = \text{DICE}(\text{Ref}(B_C), A_C) + \Sigma_{i \in C} \text{DICE}(\text{Reg}(L^i_B), L^i_A) + \|\nabla D\|$$

In some embodiments, the loss term $\|\nabla D\|$ may be replaced with alternate loss terms that are known in the art. Similarly, in some embodiments, the common liver Dice coefficient, the common lesion Dice coefficient, or both may be replaced with alternate metrics that similarly identify the common domain of the livers and lesions, respectively. For example, the alternate metrics may include overlap metrics or distance-based metrics. These alternative metrics, however, may similarly use the common domain (in the first and second term of the loss function).

In some embodiments, principal component analysis (PCA) may be used to ensure that the patient's liver is oriented in the same direction in both scans used to produce the registered scan.

Figure 4:
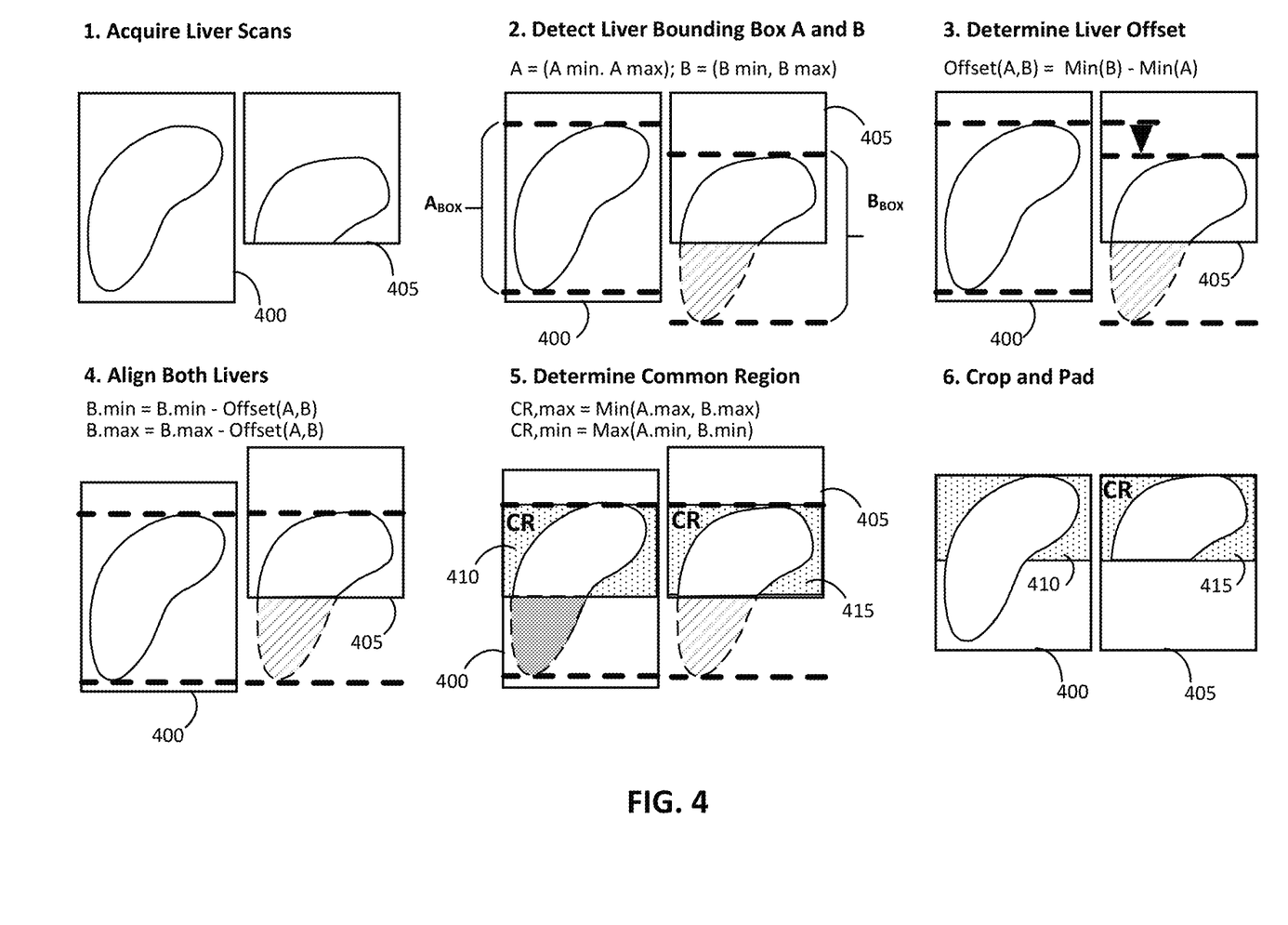
FIG. 4 illustrates an example of identifying a common liver region according to some embodiments.

FIG. 4 provides further details of identifying the common regions between two scans. As illustrated in FIG. 4, in Step 1, the liver scans (i.e., Scan 400 and Scan 405) are acquired. In this example, Scan 400 is a full scan of a patient's liver and Scan 405 is a partial scan of the patient's liver. In Step 2, liver detection is performed to identify the bounds of the patient's liver in the coordinate system of the Scans 400 and 405, such as bounding box having an upper boundary and a lower boundary. In some embodiments, the bounds are identified using a deep learning model configured to identify organs or body part, such as livers. These models are well-known in the art and, thus, are not described herein in detail. As shown in Step 2, the bounds of the patient's liver scanned in Scan 400 in the image coordinate system of Scan 400 are detected and identified as $A_{Box}=\{A\ min,\ A\ max\}$. Similarly, the bounds of the patient's liver scanned in Scan 405 in the image coordinate system of Scan 405 are detected and identified as $B_{Box}=\{B\ min,\ B\ max\}$. In this example, the bounds of the liver in both scans ($A_{min}$, $B_{min}$, $A_{max}$, $B_{max}$) are indicated in each of Scan 400 and 405 using dashed lines.

In Step 3, the offset between the patient's liver in both scans is determined based on the location of the bounds of the liver, such as via the following equation:

$$\text{Offset}(A,B)=\text{Min}(B)-\text{Min}(A).$$

It should be understood that this offset can be computed on either the lower or upper bound (e.g., based on a difference of minimums or a difference of maximums). Additionally, to cope with small discrepancies between boundary estimation, a combination of the two offset versions (e.g., the average) can be used.

In the provided example, the liver in Scan 405 is at a lower location in the scan than the liver in Scan 400 as illustrated by the downward facing arrow between the two dashed lines at the tops of the livers in Scan 400 and Scan 405.

In Step 4, the patient's liver in both Scan 400 and Scan 405 is aligned. In some embodiments, this aligned can be performed using the following equations:

$$B.\text{min}=B.\text{min}-\text{Offset}(A,B)$$

$$B.\text{max}=B.\text{max}-\text{Offset}(A,B)$$

After the patient's liver in Scan 400 and Scan 405 is aligned, common regions 410 and 415 between the two scans is determined in Step 5. The common regions (CR) 410 and 415 in each scan can be determined using the following equations:

$$CR.\text{max}=\text{Min}(A.\text{max},B.\text{max})$$

$$CR.\text{min}=\text{Max}(A.\text{min},B.\text{min})$$

In Step 6, the patient's liver is cropped and padded. For example, both Scan 400 and 405 are cropped to remove areas outside of the aligned bounding boxes and the non-common region in one of the scans (i.e., Scan 400) is used to pad the other scan (i.e., Scan 405) so that the scans have equal size or dimension. The common regions 410 and 415 are used in the loss function, disclosed above, to mask the liver region used in registration. It should be understood that the above common region identification process can be performed to partial liver scans cut at the top or bottom on either scan.

The coordinates in the example Scans 400 and 405 illustrated in FIG. 4 are comparable up to the computed offset. This is true if the coordinate system used to express the boundaries is in unit length (e.g., millimeter) or if the spacing is the same between the two scans. In the unit length case, an additional step is performed to convert (e.g., dividing by the slice spacing) the boundary in both scan 400 and 405. In the spacing case, the coordinates can be used as is (i.e., without the need for the converting step). Alternatively, in some embodiments, spacing can be enforced to be the same by resampling input exams.

Figure 5:
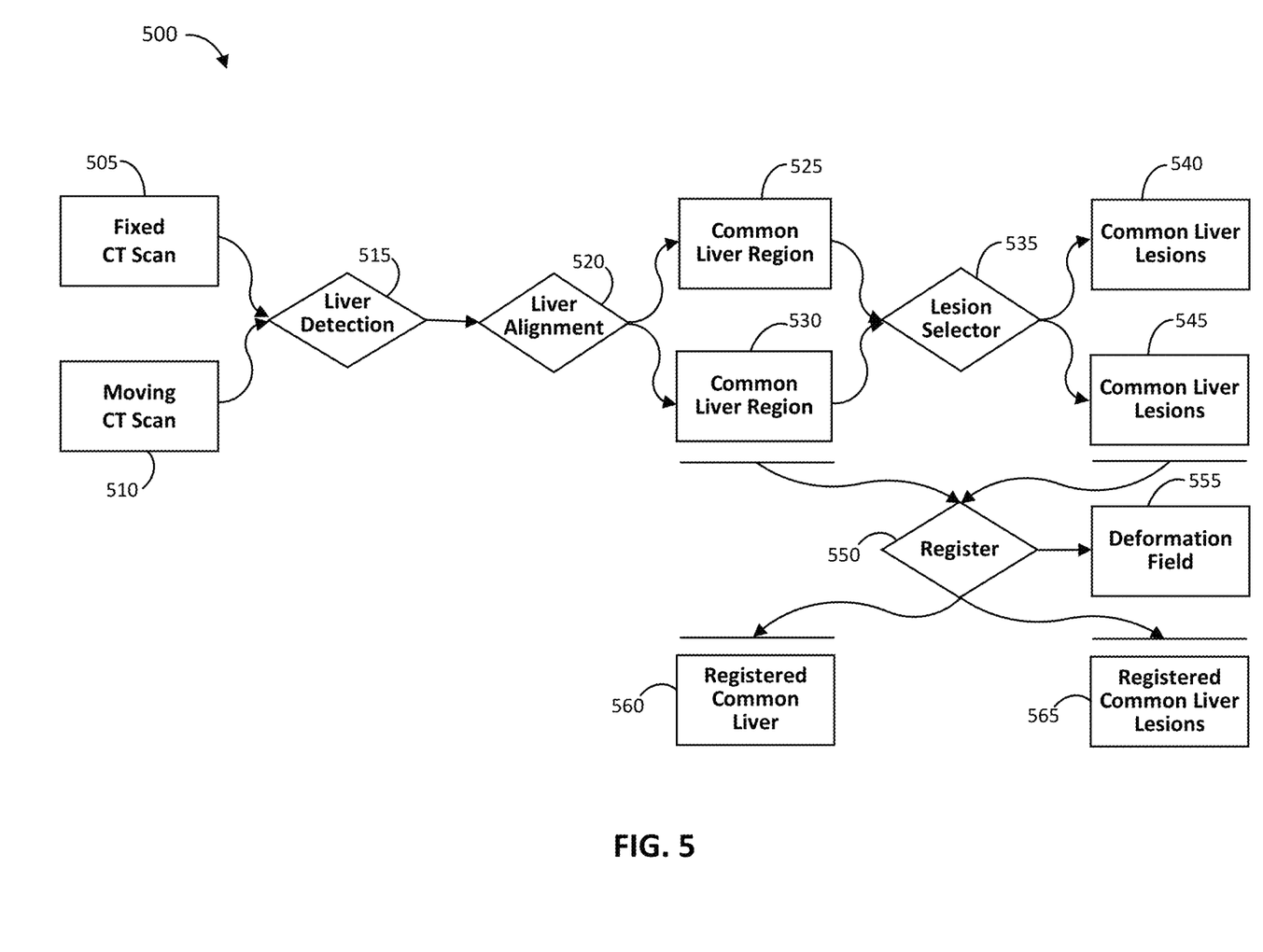
FIG. 5 is a flowchart illustrating a method of training a model for registering images according to some embodiments.

The above common region identification process can be used both as part of performing image registration as well as training a model (e.g., employing a deep learning algorithm) to perform the image registration. For example, to train a model to perform image registration on aligned, common liver regions, the model must be trained using such images. FIG. 5 is a flow chart illustrating a method 500 of training a model, such as a neural network, for registering CT scans as described herein according to one embodiment. The method 500 is described with respect two image scans but it should be understood that the training process can be performed for multiple sets of image scans to form a training dataset for the model.

As illustrated in FIG. 5, the method 500 includes detecting a liver in each of two CT scans or images (e.g., CT Scan 505 and CT Scan 510) (at 515). In this example, Scan 505 can be referred to as a fixed scan and Scan 510 can be referred to as a moving scan, wherein Scan 510 (representing an image with potential patient movement) will be registered to Scan 505. Scan 505 and Scan 510 were acquired from a patient at different time frames. As noted above, liver detection may be performed using a known liver detection model or algorithm that outputs at least a bounding box for the liver captured in each of the scans.

After the bounds of the livers are determined (at 502), the livers of Scan 505 and 510 are aligned (at 520), such as by using the equation discussed above in Step 4 of FIG. 4. With the livers aligned, a Common Liver Region 525 and a Common Liver Region 530 are identified in each of Scan 505 and Scan 510, such as by using the equation discussed above in Step 5 of FIG. 4.

From the Common Liver Regions 525 and 530, a set of common lesions is selected within the regions (at 535), wherein each selected lesion in the set exists in both the Common Liver Region 525 and the Common Liver Region 530. In other words, a set of Common Liver Lesions 540 is determined for Common Liver Region 525 and a set of Common Liver Lesions 545 is determined for Common Liver Region 530, wherein each lesion in one of these sets is also included in the other set.

As illustrated in FIG. 5, the Common Liver Region 525, the Common Liver Region 530, the Common Liver Lesions 540, and the Common Liver Lesions 545 are input to the registration model to register the Common Liver Region 525 and the Common Liver Region 535 (at 550). In particular, the registration model generates a Deformation Field 555 based on the Common Liver Region 525 and the Common Liver Region 530. The Deformation Field 555 is used to register Common Liver Region 530 to Common Liver Region 525 and the identified lesions (i.e., Common Liver Lesions 545 to Common Liver Lesions 540). Accordingly, as illustrated in FIG. 5, the registration model outputs a Registered Common Liver Region 560 and a Registered Common Liver Lesions 565. As part of the training process, the registration model uses the generated Deformation Field 555, the Registered Common Liver Region 560, the Common Liver Region 525, the Registered Common Liver Lesions 565, and the Common Liver Lesions 540 to compute a registration loss function (see, e.g., above loss function including a common liver Dice coefficient and a common lesion Dice coefficient), which is minimized using deep learning optimization to find registration algorithm parameters for the registration model.

After the registration model is trained, the model can be used to register two images or scans (e.g., without the need for lesion selection as performed during the training process). For example, FIG. 6 is a flow chart illustrating a method 600 of performing image registration using common liver regions using the model trained according to the method 500.

Figure 6:
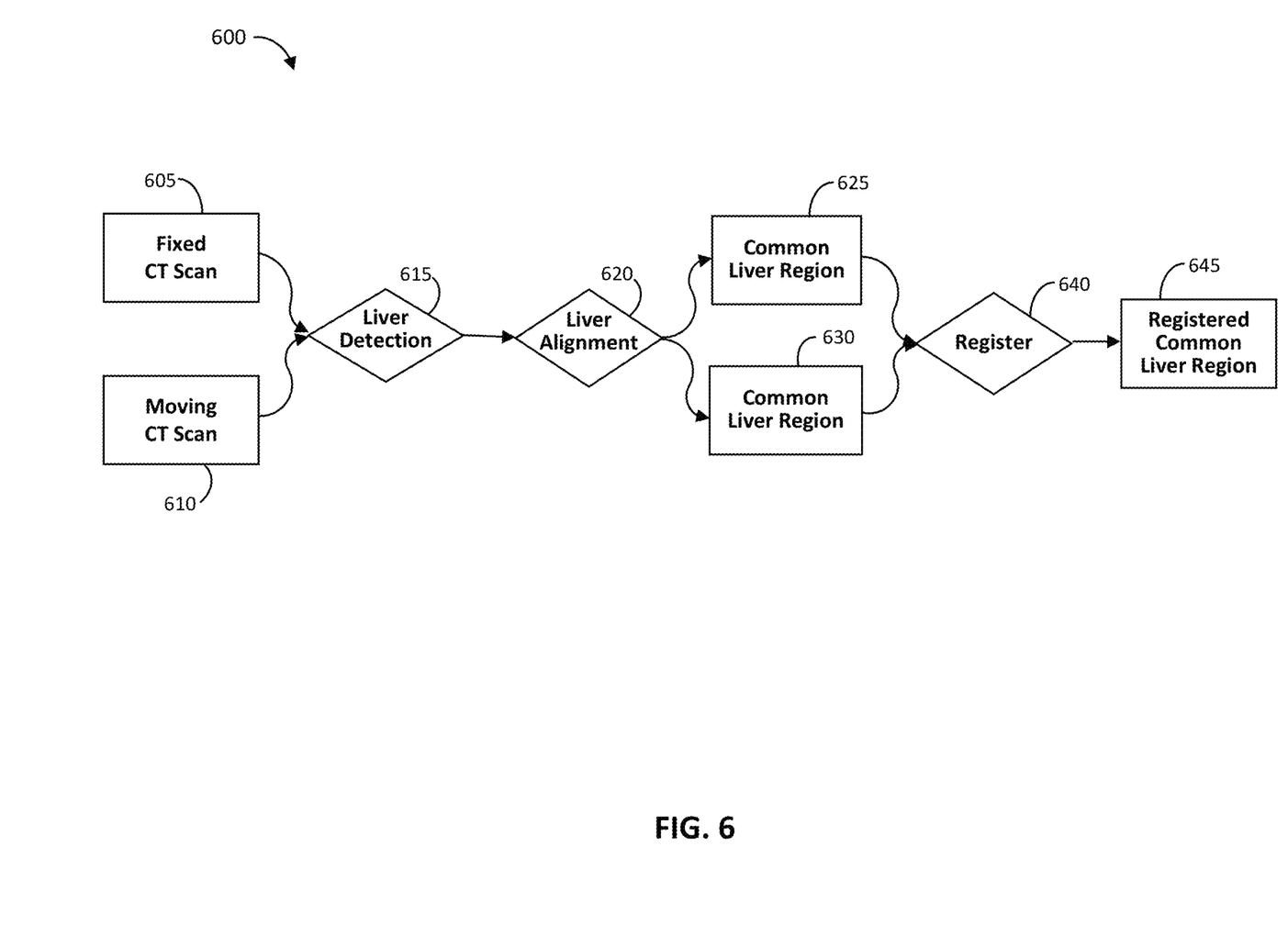
FIG. 6 is a flowchart illustrating a method of inferring images according to some embodiments.

As illustrated in FIG. 6, the method 600 includes detecting a liver in each of two CT scans or images (e.g., CT Scan 605 and CT Scan 610) (at 615). In this example, Scan 605 can be referred to as a fixed scan and Scan 610 can be referred to as a moving scan, wherein Scan 610 (representing an image with potential patient movement) will be registered to Scan 605. Scan 605 and Scan 610 were acquired from a patient at different time frames. As noted above, liver detection may be performed using a known liver detection model or algorithm that outputs at least a bounding box for the liver captured in each of the scans. As noted above, in some embodiments, the bounding box may identify an estimated physical liver boundary.

After the bounds of the livers are determined (at 615), the livers of Scan 605 and 610 are aligned (at 620), such as by using the equation discussed above in Step 4 of FIG. 4. With the livers aligned, a Common Liver Region 625 and a Common Liver Region 630 are identified in each of Scan 605 and Scan 610, such as by using the equation discussed above in Step 5 of FIG. 4.

As illustrated in FIG. 6, the Common Liver Region 625 and the Common Liver Region 630 are input to the registration model (trained as described above) to generate a Registered Common Liver 645 (i.e., register Scan 610 to Scan 605).

As noted above, by focusing on the common liver regions and matching lesions or other landmarks within this common liver region, the Registered Common Liver 645 more accurately reflects a size, shape, and volume of the patient's liver and lesion as compared to other image registration techniques.

Figure 7:
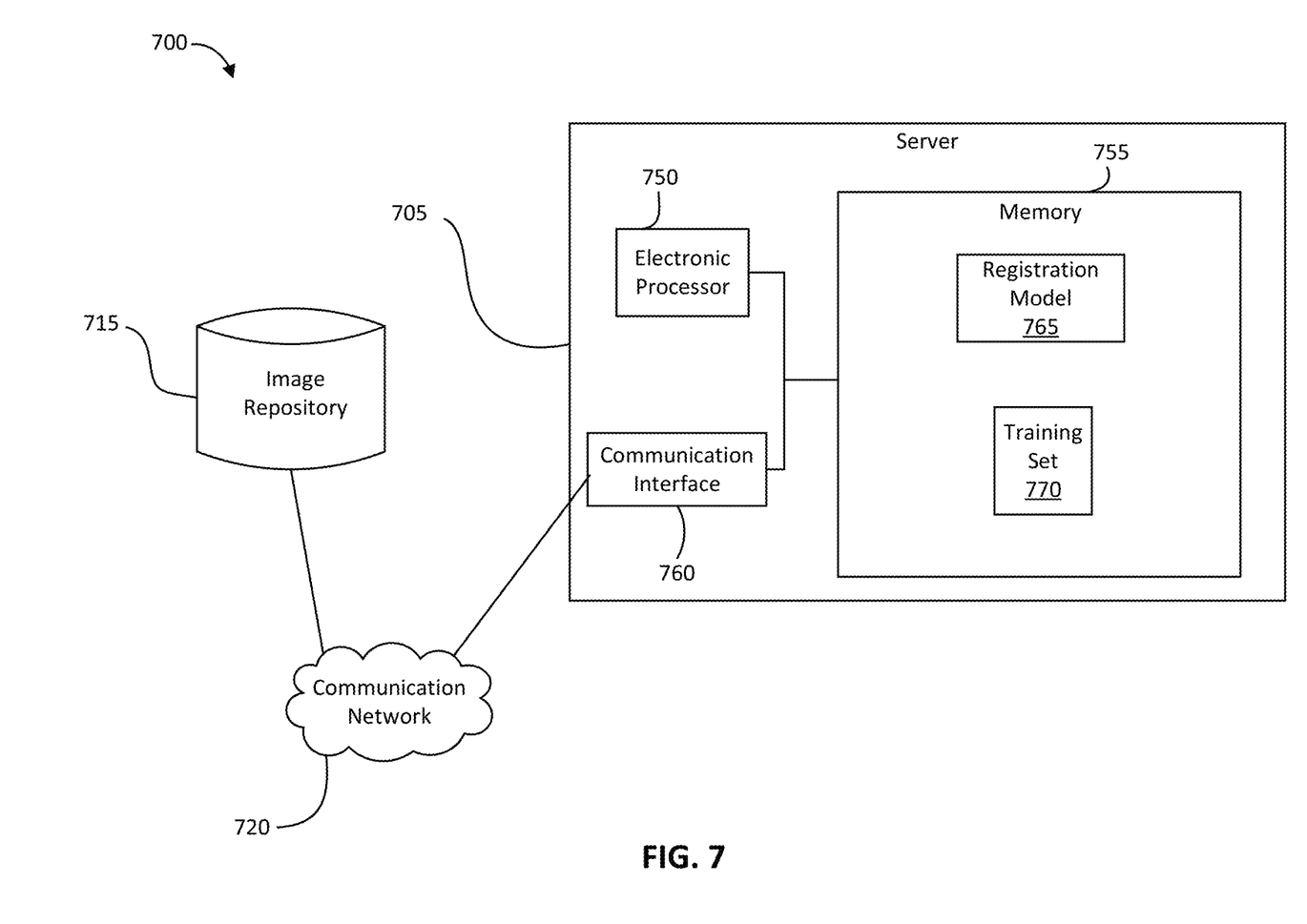
FIG. 7 illustrates a block diagram of a system for performing image registration according to some embodiments.

It should be understood that the functionality described herein can be performed via one or more computing devices, such as one or more servers. For example, FIG. 7 illustrates a system 700 for training a registration model, for example, a neural network, to perform image registration as described herein. This same system 700 may also be used to perform image registration using the model as trained. However, in other embodiments, the trained registration model can be applied or used by a different system than the system used to train the mode.

As illustrated in FIG. 7, the system 700 includes a server 705 and an image repository 715. The server 705 and the image repository 715 communicate over one or more wired or wireless communication networks 720. Portions of the communication networks 720 may be implemented using a wise area network, such as the Internet, a local area network, such as a Bluetooth™ network or Wi-Fi, and combinations or derivatives thereof. It should be understood that the system 700 may include more or fewer servers and the single server 705 illustrated in FIG. 7 is purely for illustrative purposes. For example, in some embodiments, the functionality described herein is performed via a plurality of servers in a distributed or cloud-computing environment. Also, in some embodiments, the server 705 may communicate with multiple image repositories. Furthermore, in some embodiments, an image repository may be combined with the image repository 715. Also, in some embodiments, the components illustrated in system 700 may communicate through one or more intermediary devices (not shown).

In some embodiments, the image repository 715 stores medical images, such as, for example, CT image scans. For example, the image repository 715 may be, for example, a picture archiving and communication system (PACS), a cloud storage environment, or the like.

As illustrated in FIG. 7, the server 705 includes an electronic processor 750, a memory 755, and a communication interface 760. The electronic processor 750, the memory 755, and the communication interface 760 communicate wirelessly, over wired communication channels or buses, or a combination thereof. The server 705 may include additional components than those illustrated in FIG. 7 in various configurations. For example, in some embodiments, the server 705 includes multiple electronic processors, multiple memory modules, multiple communication interfaces, or a combination thereof. Also, it should be understood that the functionality described herein as being performed by the server 705 may be performed in a distributed nature by a plurality of computers located in various geographic locations. For example, the functionality described herein as being performed by the server 705 may be performed by a plurality of computers included in a cloud computing environment.

The electronic processor 750 may be, for example, a microprocessor, an application-specific integrated circuit (ASIC), and the like. The electronic processor 750 is generally configured to execute software instructions to perform a set of functions, including the functions described herein. The memory 755 includes a non-transitory computer-readable medium and stores data, including instructions executable by the electronic processor 750. The communication interface 760 may be, for example, a wired or wireless transceiver or port, for communicating over the communication network 720 and, optionally, one or more additional communication networks or connections.

As illustrated in FIG. 7, the memory 455 of the server 705 stores a registration model 765, may include a neural network. As also illustrated in FIG. 7, the memory 455 also stores a training set 770, which as described above, may include a plurality of CT scans (e.g., retrieved from the image repository 715) used to train the registration model 765. Although not illustrated in FIG. 7, the memory 755 also stores instructions executable by the electronic processor 750 to train the registration model 765 using the training set 770. The memory 755 may store additional instructions, such as, for example, instructions for testing the registration model 765, applying the registration model 765 (as trained) to perform image registration between two or more scans, or a combination thereof.

Embodiments described herein provide methods and systems for performing image registration by focusing on common regions between two scans as well as landmarks (e.g., lesions) in each common region. Thus, as compared to surface-based image registration, embodiments described herein better preserve the shape of the patient's liver and reconstruct a location of one or more lesions within the liver. The methods and systems can include a registration model that trained using a loss function that focuses on common regions of scans (e.g., computed using upper and lower boundary estimation) as well as lesions visible within these regions, wherein the loss function (including a common liver Dice coefficient and a common lesion Dice coefficient) is minimized during such training using deep learning optimization.

It should be understood that although the methods and systems are described above using CT liver scans, the methods and systems described herein can be applied to other types of images and other labeled organic structures. For example, the methods and systems described herein can be applied to 2D/3D images, magnetic resonance images (MRIs), positron emission tomography scans (PET scans), digital breast tomosynthesis scans (DBT scans), and the like, and can be used to with various labeled organic structures, such as, for example, vessels, vessel-tree nodes, ducts, and the like. Also, the methods and systems described herein can be applied to any number of scans. Additionally, unlike other systems that require prior information to determine a registration region, such as, for example, lesion size or location, embodiments described herein automatically determine a registration region. Accordingly, embodiments described herein can be used to register images regardless of the presence of prior scans, reports, or annotations. Accordingly, embodiments described herein are applicable to initial as well as consecutive scans. With respect to the present application, the terms "lesion" and "tumor" are used interchangeably. Additionally, the terms "scan" and "image" are used interchangeably.

Various features and advantages of the embodiments are set forth in the following claims.

What is claimed is:

1. A computer-implemented method of performing image registration, the method comprising: receiving a first image and a second image, the first image and the second image acquired from a patient at different times; in each of the first image and the second image: detecting an upper boundary of an imaged object in an image coordinate system, and detecting a lower boundary of the imaged object in the image coordinate system; based on the upper boundary and the lower boundary of each of the first image and the second image, cropping and padding at least one of the first image and the second image to create an aligned first image and an aligned second image; executing a registration model on the aligned first image and the aligned second image to compute a deformation field between the aligned first image and the aligned second image; wherein detecting the upper boundary of the imaged object in each of the first image and the second image includes detecting the upper boundary in each of the first image and the second image using a deep learning model; and wherein detecting the lower boundary of the imaged object in each of the first image and the second image includes detecting the lower boundary in each of the first image and the second image using a deep learning model.

2. The method of claim 1, wherein receiving the first image and the second image includes receiving a first three-dimensional (3D) image of a liver of the patient and a second 3D image of the liver of the patient.

3. The method of claim 2, wherein the first 3D image is a computed tomography (CT) image and the second 3D image is a CT image.

4. The method of claim 2, wherein the first 3D image is a magnetic resonance (MR) image and the second 3D image is a MR image.

5. The method of claim 1, wherein executing the registration model includes executing a deep learning model trained using a loss function, wherein a first term of the loss function includes a common portion of the imaged object within the aligned first image and the aligned second image.

6. The method of claim 5, wherein a second term of the loss function includes on one or more lesions visible in both the aligned first image and the aligned second image.

7. A system for performing image registration, the system comprising: an electronic processor configured to: receive a first image and a second image, the first image and the second image acquired from a patient at different times, in each of the first image and the second image: detect an upper boundary of an imaged object in an image coordinate system, and detect a lower boundary of the imaged object in the image coordinate system, based on the upper boundary and the lower boundary of each of the first image and the second image, crop and pad at least one of the first image and the second image to create an aligned first image and an aligned second image, execute a registration model on the aligned first image and the aligned second image to compute a deformation field between the aligned first image and the aligned second image; wherein detecting the upper boundary of the imaged object in each of the first image and the second image includes detecting the upper boundary in each of the first image and the second image using a deep learning model; and
wherein detecting the lower boundary of the imaged object in each of the first image and the second image includes detecting the lower boundary in each of the first image and the second image using a deep learning model.

8. The system of claim 7, wherein the first image is a first three-dimensional (3D) image of a liver of the patient and the second image is a second 3D image of the liver of the patient.

9. The system of claim 7, wherein the electronic processor is configured to detect the upper boundary and the lower boundary of the imaged object in each of the first image and the second image via a deep learning model.

10. The system of claim 7, wherein the electronic processor is configured to execute the registration model by executing a deep learning model trained using a loss function, a first term of the loss function including a common portion of the imaged object within the aligned first image and the aligned second image.

11. The system of claim 10, wherein a second term of the loss function includes one or more lesions visible in both the aligned first image and the aligned second image.

12. Non-transitory computer readable medium storing instructions that, when executed by an electronic processor, perform a set of functions, the set of functions comprising: receiving a first image and a second image, the first image and the second image acquired from a patient at different times; in each of the first image and the second image: detecting an upper boundary of an imaged object in an image coordinate system, and detecting a lower boundary of the imaged object in the image coordinate system; based on the upper boundary and the lower boundary of each of the first image and the second image, cropping and padding at least one of the first image and the second image to create an aligned first image and an aligned second image; and executing a registration model on the aligned first image and the aligned second image to compute a deformation field between the aligned first image and the aligned second image;
wherein detecting the upper boundary and the lower boundary of the imaged object in each of the first image and the second image includes detecting the upper boundary in each of the first image and the second image using a deep learning model.

13. The non-transitory computer readable medium of claim 12, wherein receiving the first image and the second image includes receiving a first three-dimensional (3D) image of a liver of the patient and a second 3D image of the liver of the patient.

14. The non-transitory computer readable medium of claim 13, wherein the first 3D image is one selected from a group consisting of a computed tomography (CT) image and a magnetic resonance (MR) image and the second 3D image is one selected from a group consisting of a CT image and a MR image.

15. The non-transitory computer readable medium of claim 12, wherein executing the registration model includes executing a deep learning model trained using a loss function, wherein a first term of the loss function includes a common portion of the imaged object within the aligned first image and the aligned second image.

16. The non-transitory computer readable medium of claim 15, wherein the loss function includes one or more lesions visible in both the aligned first image and the aligned second image.

\* \* \* \* \*